(12) United States Patent
Williams et al.

(10) Patent No.: US 9,039,636 B2
(45) Date of Patent: May 26, 2015

(54) DEVICES AND METHODS FOR ENHANCED CELLULAR SAMPLE TRANSFER

(75) Inventors: Donald Williams, Newport Beach, CA (US); Michael Friedl, Laguna Hills, CA (US)

(73) Assignee: Resolution Biomedical, Inc., Tustin, CA (US)

( * ) Notice: Subject to any disclaimer, the term of this patent is extended or adjusted under 35 U.S.C. 154(b) by 301 days.

(21) Appl. No.: 13/360,263

(22) Filed: Jan. 27, 2012

(65) Prior Publication Data
US 2012/0196313 A1    Aug. 2, 2012

Related U.S. Application Data

(60) Provisional application No. 61/457,198, filed on Jan. 27, 2011.

(51) Int. Cl.
  *A61B 5/00*   (2006.01)
  *A61B 10/02*  (2006.01)
  *A61M 1/00*   (2006.01)

(52) U.S. Cl.
  CPC .............. *A61B 10/02* (2013.01); *A61M 1/0001* (2013.01)

(58) Field of Classification Search
  CPC ............... A61B 10/02; A61B 10/0045; A61B 2010/0074; A61B 10/0216; A61M 1/0001
  USPC ........... 600/569, 570, 572, 579; 604/317, 403
  See application file for complete search history.

(56) References Cited

U.S. PATENT DOCUMENTS

| | | | | |
|---|---|---|---|---|
| 4,675,110 A | * | 6/1987 | Fay | 210/436 |
| 4,964,413 A | * | 10/1990 | Losada et al. | 600/579 |
| 5,422,273 A | * | 6/1995 | Garrison et al. | 435/307.1 |
| 5,830,154 A | * | 11/1998 | Goldstein et al. | 600/572 |
| 6,291,234 B1 | * | 9/2001 | Raz et al. | 435/309.1 |
| 7,377,027 B2 | * | 5/2008 | Mayer | 29/709 |
| 7,767,448 B2 | * | 8/2010 | Yong | 435/309.1 |

* cited by examiner

*Primary Examiner* — Max Hindenburg
(74) *Attorney, Agent, or Firm* — Knobbe, Martens, Olson & Bear, LLP

(57) ABSTRACT

Described are embodiments of a biological specimen collection transfer and container system and method for handling and processing specimens of cellular, and related particulate matter, directly into a vial or other like container. The vial, or container, assembly includes a series of ridges, protrusions, or like engagement members, that extend from the inside of the vial or container. Application of an external force between the collection apparatus and the engagement members contained within the vial, or container, results in an increased amount of cells, cellular structures, related material, and other particulates to transfer from the collection apparatus to the vial, or like container, thereby improving the sample yield and processing effectiveness of the sample in order to increase diagnostic utility.

13 Claims, 3 Drawing Sheets

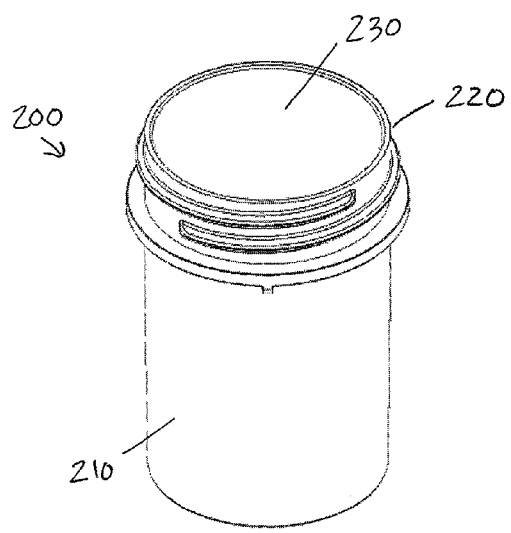
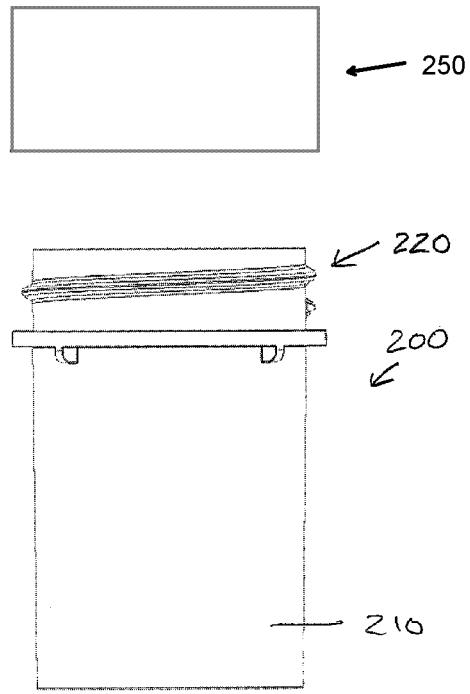
FIG. 1
FIG. 2
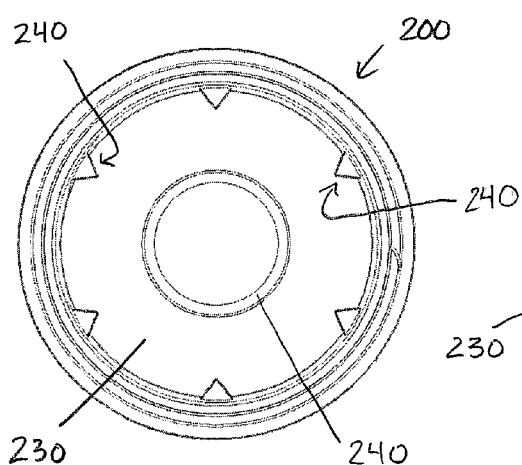
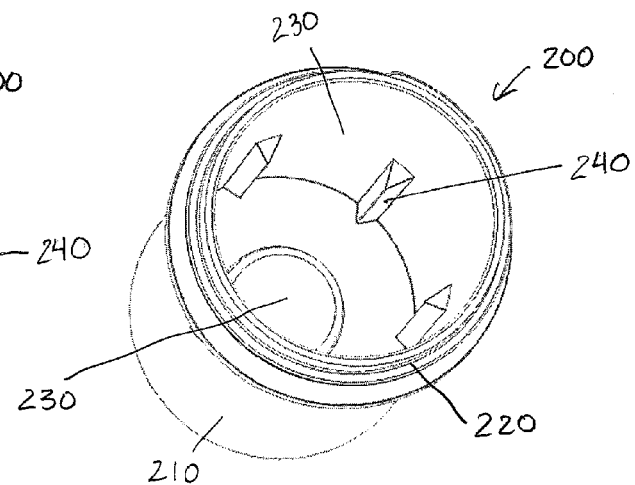
FIG. 3
FIG. 4

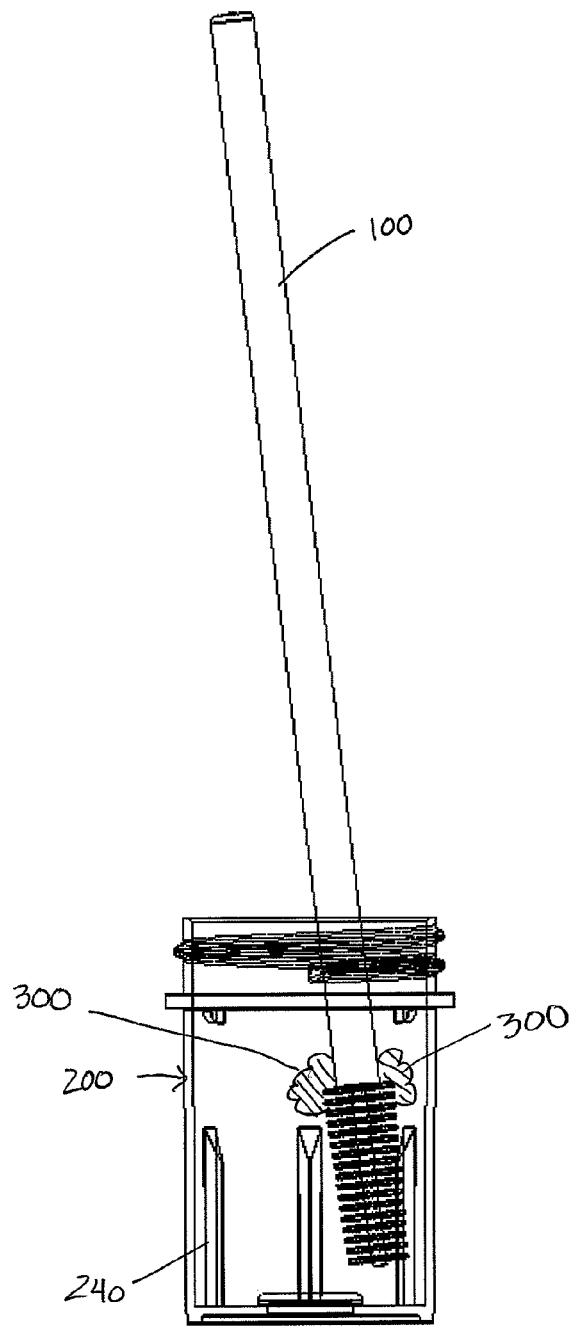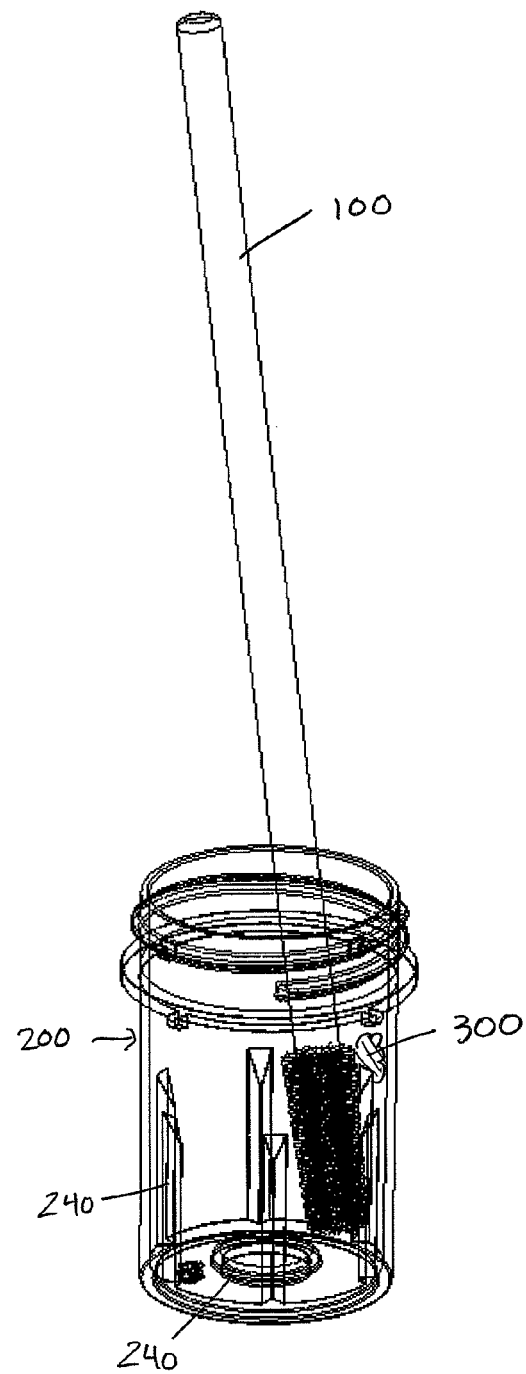
FIG. 5                    FIG. 6

DEVICES AND METHODS FOR ENHANCED CELLULAR SAMPLE TRANSFER

CROSS-REFERENCE TO RELATED APPLICATIONS

This application claims the benefit and priority under 35 U.S.C §119(e)(1) of U.S. provisional application No. 61/457,198, filed Jan. 27, 2011, which application is incorporated herein by reference in its entirety.

BACKGROUND

1. Field

Embodiments of the invention are directed to an apparatus and/or a method for collecting, transferring, and processing biological specimens, including collecting cells, cellular materials, and other matter suitable for use in cytology protocols and diagnostic tests.

2. Description of the Related Art

In a wide variety of diagnostic assays, the ability to separate matter, typically cells, cellular matter, and particulate matter, from a fluid can be important for the enablement of testing for the presence or absence of substances and other diagnostic materials contained in the fluid. Oftentimes, sample preparation obscures the target matter, decreasing the utility of the sample for detection and/or diagnostic analysis. Such shortcomings are particularly acute in the field of cytological examinations, where cells, cellular structures, and related components vital to useful diagnostic examination are lost during sample preparation, transport, and testing phases.

Cytological examination of a sample typically begins with obtaining a specimen or specimens of cells and related material from a host, which is typically accomplished by brushing, scraping, or swabbing a body area, as in the case of cervical, oral, and anal specimens, or by collecting body fluids such as urine, blood, or plasma, or by collecting fluids from such body areas as the bladder, vaginal cavity, anal cavity, oral cavity, chest cavity, or spinal column, or by fine needle aspiration or fine needle biopsy of those and/or other areas of the body. A significant challenge for such cytological preparations is transferring as many cells, and related materials, from the fluid, and/or body area sampled, to collection and/or processing containers and finally to slides or other devices for diagnostic analysis. Given that diagnostic accuracy of both microbiologic and cytologic assays depends heavily on microscopic examination of cells, cellular structures, and related materials, adequate sample retention and transfer to preservative or processing fluids, and ultimately to viewing platforms and devices, can be important.

Currently, biological samples and specimens are collected for liquid-based cytological examination by using various devices, such as brushes, smears, spatulas, swabs and/or other collection devices, to transfer cells, and related materials, to a transfer or preservative liquid, which is then contacted with slides or other viewing platforms or devices for diagnostic analysis. Current methods, however, suffer from poor transfer rates of such cells and related materials to the transfer or preservative liquids. Such low transfer rates can result in poor, or even complete failure of, diagnostic utility and results.

Many of the cell collection, transfer, and analysis situations mentioned above also relate to challenges faced during various cytology and related diagnostic methods such as Human Papillomavirus (HPV), GC/Chlamydia, and other reflex testing procedures and assays.

In view of the foregoing, there is a need for improved methods and devices to increase the transfer rates of cells, cellular structures, and related materials, from collection devices to transfer or preservative liquids, and ultimately then to slides or other viewing platforms or devices for useful diagnostic analysis. One of the challenges in producing useful diagnostic samples for liquid-based cytology is ensuring that a suitable amount of cells, and other specimen materials, are transferred from collection apparati to vials, or like containers, for further processing. Other challenges include potential cross-contamination of samples and loss of materials during transfer, preparation, and analysis processes. Embodiments of the present invention may mitigate those challenges.

SUMMARY

In one embodiment of the present invention, a vial-based apparatus and a method of collecting specimens of biologic fluid, including cellular specimens, is disclosed for use in liquid-based cytology analysis. In a wide variety of technologies, the ability to capture significant cellular material and transfer such specimen material into a transport vial containing preservative, can be an important step in the ability to test for the presence of substances in the sample.

In one embodiment, a biological specimen collection vial includes one or more interior surface features embedded on one or more interior surfaces of the vial configured for physical agitation between a collection apparatus and one or more of said interior surface in order to more effectively release cellular specimen material.

In one embodiment, the one or more interior surface features are arranged in a pattern on the interior of the vial and are spaced between 5 and 10 millimeters apart. In one embodiment, the one or more interior surface features are arranged in a pattern on the interior of the vial and are spaced more than 10 millimeters apart. In one embodiment, the one or more interior surface features are arranged in a vertical pattern on the interior of the vial and are spaced between 5 and 10 millimeters apart. In one embodiment, the one or more interior surface features are arranged in a vertical pattern on the interior of the vial and are spaced more than 10 millimeters apart. In one embodiment, a method includes the step of transferring sample cellular material into the collection vial is accomplished by contacting a collection device with at least one interior surface feature. In one embodiment, the method includes detaching a cap from the vial during processing of the sample. In one embodiment, a method includes attaching the cap to the vial during a sample collection, the cap comprising a hole in the top of the cap with a cover that allows the sample to be transferred into other containers for analysis.

In one embodiment, a method of obtaining an aliquot of a liquid-based biological sample disposed in a collection apparatus, includes the steps of contacting a collection apparatus with at least one interior surface feature in a vial in order to transfer the aliquot of the biological sample from the collection apparatus into the vial, and removing the collection apparatus from the vial.

In one embodiment, the method is further configured for harvesting cells and related cellular materials from the collection apparatus in a liquid-based system, further including providing the vial at least partially filled with liquid, placing the collection apparatus in said vial so that a portion thereof is submerged in said liquid, positioning said collection apparatus within said vial, and moving said collection apparatus so that it physically contacts said at least one interior surface feature. In one embodiment, the collection apparatus is selected among the group consisting of an endocervical brush, a swab, and a broom.

Further aspects and features of the present invention will be apparent to persons of ordinary skill in the art, based upon the description provided herein.

BRIEF DESCRIPTION OF THE DRAWINGS

Example embodiments disclosed herein are illustrated in the accompanying schematic drawings, which are for illustrative purposes only. The drawings are not necessarily drawn to scale, unless otherwise stated as such, or necessarily reflect relative sizes of illustrated aspects of the embodiments.

FIG. 1 schematically illustrates an isometric front view of a collection vial according to one embodiment of the present invention.

FIG. 2 schematically illustrates side view of the collection vial according to FIG. 1.

FIG. 3 schematically illustrates top of the collection vial according to FIG. 1.

FIG. 4 schematically illustrates an isometric top view of the collection vial according to FIG. 1.

FIG. 5 schematically illustrates a side view of a collection vial with a collection device 100 according to one embodiment.

FIG. 6 schematically illustrates a side elevated isometric view of the collection vial with the collection device according to FIG. 5.

DETAILED DESCRIPTION OF THE PREFERRED EMBODIMENTS

Figure 7:
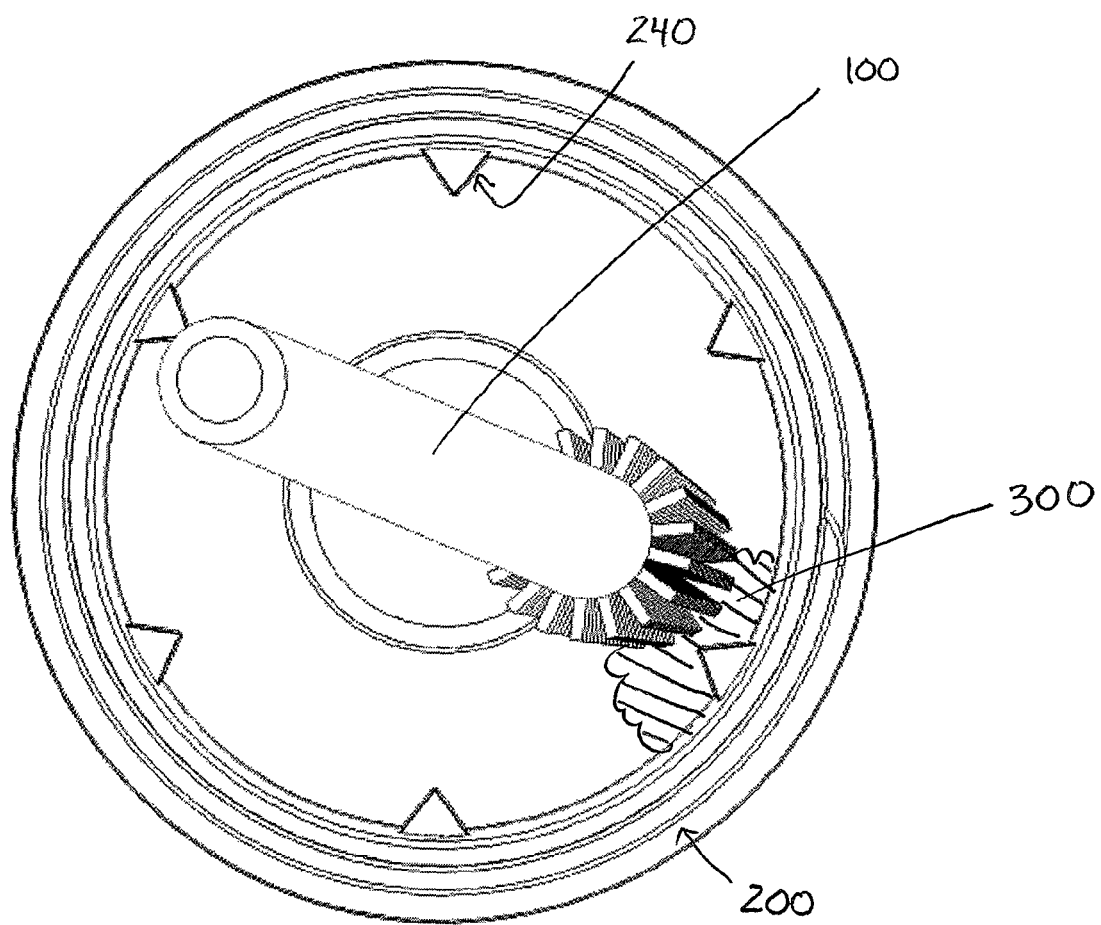
FIG. 7 schematically illustrates a top view of the collection vial with the collection device according to FIG. 5.

Described are improved methods and devices for collecting, transferring, handling, and processing cells, cellular structures, and related material specimens. One embodiment is directed to liquid-based cytology, where cells are collected from the host with, for example, a collection brush, spatula, or swab, or other collection apparatus, and said apparatus is inserted into a vial, or like container. The container can optionally contain a liquid solution. In one embodiment, a vial, or like container, has a ribbed inner surface, or contains other protrusions, which allow the collection apparatus to more effectively release collected cells, and other materials, into the container by physically contacting the collection apparatus against the ribs, or other protrusions, located on the inside surfaces of the vial, or other container. The cover to the vial, or like container, can be optionally sealed after materials are transferred from the collection apparatus. In one embodiment of the invention, the cover of the vial, or like container, can be manipulated in order to allow a portion of the sample to be transferred to other containers, such as centrifuge tubes, etc., for further processing. The ribbed, or otherwise protruded, inner surface of the vial, or like container, allows for increased amounts of desired cells and other sample material to be transferred from the collection apparatus into the vial, or like container. The sealed cover of the vial, or like container, may contribute to: (i) preventing cross-contamination, (ii) preventing airborne contaminants from mixing with the sample, and/or (iii) reducing potential evaporation of fluids.

Cytological examination typically begins with the collection of a sample 300, which can include cells, and related material, which can be accomplished, for example, by scraping or brushing an area, as in the case of cervical, oral, and anal samples, or by collecting bodily fluids such as those obtained from the bladder, vaginal cavity, oral cavity, chest cavity, or spinal column, or by aspiration of those and/or other body areas. In various embodiments, a collection device 100 is used to take a sample 300 from a body, and the sample 300 is placed in a collection vial 200. In various embodiments, the collection device 100, is a cervical brush, swab, or broom, or other collection mechanism. In various embodiments, a collection vial 200 is a vial, a container, capsule, box, storage device, or other device for holding the sample 300. In many of these endeavors, the collection device 100 is inserted into the collection vial 200, and shaken or stirred to transfer sample 300 cellular material into a liquid medium or media. However, efficiently and effectively transferring such cellular material to the collection vial 200 can be a limiting factor. The accuracy of diagnosis and the preparation of interpretable specimens from samples 300 depend in part upon adequate cell specimen transfer.

Currently, biological samples 300 are collected for liquid-based cytology processing and examination using vials, or like containers, with smooth inner surfaces. These vials, or like containers, typically contain a solution for preserving the cytology specimen during shipment from the collection site to the cytology laboratory. The samples 300 or specimens collected from the body using a brush, smear, swab, or spatula are also typically preserved in containers with fixatives (e.g., alcohol-based solutions) prior to transferring cell samples onto a microscope slide for staining and analysis.

Specimen containers are known that allow a liquid-based biological specimen to be processed in special equipment, and may be specially configured with aperture covers and adaptors that are designed to mate with filters or suction equipment used to aspirate liquid from the container. If the processing is done by automated equipment, special handling devices are required to carry out the process and disassembly of the component parts may be required. The machinery must be cleaned in each use to prevent cross-contamination. The machine-based systems add complexity, time and material, and cost to the processing required prior to the actual cytology examination.

With reference to FIGS. 1-4, one embodiment of a specimen vial 200 is designed for manual liquid-based transport and processing, and to maximize cell sample 300 or specimen collection and transfer. The vial 200 contains a simple cover (not illustrated) that can be removed at the point-of-care site (doctor's office, clinic, hospital, etc.), allowing easy access to the contents within the vial 200. In one embodiment, the vial 200 includes an exterior surface 210, a cover interface 220, an interior surface 230, and one or more interior surface features 240. In various embodiments, the interior surface feature 240 is a rib, protrusion, depression, wing, projection, surface finish, friction surface, mesh, or other sample engaging feature. After the sample 300 is collected, the collection device 100 or apparatus can be rubbed against the interior surface feature 240 on the inner surface of the vial to extract and collect sample 300 specimens. The cover is then replaced to seal the vial 200, which may then be sent out for processing.

In various embodiments, interior surface features 240 can be ribbing, ridges, or protrusions may be horizontal, vertical, or slanted. In various embodiments, the interior surface features 240 can have pocking, ribbing, ridges, and/or protrusions that may be reticulated, random, or designed, or be a combination of some or all of those. In one embodiment, the series of ridges, protrusions, or like engagement members, run vertically in the vial 200, with each rib approximately 5 millimeters apart. In another embodiment, the series of ridges, protrusions, or like engagement members, run vertically in the vial, with each rib approximately 10 millimeters apart. In another embodiment, the series of ridges, protrusions, or like engagement members, run vertically in the vial, with each rib more than 10 millimeters apart.

With reference to FIGS. 5-7, in various embodiments, the vial 200 can be opened and all, or a portion, of the sample 300 material can be poured into another container such as a centrifuge tube, in order to spin down the cellular material. In one embodiment, the vial lid cover flips open, thereby exposing an opening to pour a volume of sample 300 for transfer or further processing. In contrast to prior art specimen vials and containers, one embodiment of the vial cover is not removed and the vial 200 does not remain open, thus reducing possibility of cross contamination or airborne contaminants.

Described are embodiments of a biological specimen collection transfer and container system and methods for handling and processing specimens of cellular, and related particulate matter, directly into a vial 200 or other like container. The vial 200 assembly includes a series of interior surface features 240, and in various embodiments the interior surface features 240 are ridges, protrusions, or like engagement members, that extend from the inside of the vial 200, or any combination thereof. Application of an external force between the collection apparatus 100 and the interior surface feature 230 engagement members contained within the vial 200 results in an increased amount of sample 300 cells, cellular structures, related material, and other particulates to transfer from the collection apparatus to the vial 200 thereby improving the sample 300 yield and processing effectiveness of the sample 300 in order to increase diagnostic utility.

In one embodiment, a biological sample vial 200 for holding the biological sample 300 includes a cap 250 configured to removably seal the vial 200, wherein the vial 200 contains a series of ridges, protrusions, or like engagement members, that extend from the inside wall of the vial or container.

In another aspect, embodiments of the disclosed inventions include a method of transferring a biological sample 300 from a collection apparatus 100 to a vial 200 wherein the vial 200 contains a series of ridges, protrusions, or like engagement members, that extend from the inside of the vial or container, designed to increase the amount of the biological sample that can be obtained from the collection apparatus. The method may also optionally comprise capping the vial or container after transferring the biological sample 300 from the collection apparatus 100.

In another embodiment, the method comprises obtaining a biological sample 300 with a collection apparatus 100 such as a brush, swab, or broom, and transferring the biological sample 300 to a container 200, the container comprising a chamber containing a series of ridges, protrusions, or like engagement members, that extend from the inside of the container 200.

In some embodiments, the container 200 may further comprise a wall in which a series of ridges, protrusions, or like engagement members extend outward from the surface of the wall, and the method may further comprise contacting the collection apparatus 100 with the ridges, protrusions, or like engagement members embedded in the container wall, thereby causing the biological sample 300 to transfer from the collection apparatus 100 to the chamber of the container 200.

In still another aspect, embodiments of the invention include a method for the application of an external force between the collection apparatus 100 and the engagement members 240 contained within the vial 200, or container, resulting in an increased amount of sample 300 cells, cellular structures, related material, and other particulates to transfer from the collection apparatus to the vial, or like container, thereby improving the sample yield.

In yet another aspect, embodiments of the invention include a method for the application of an external force between the collection apparatus 100 and the engagement members 240 contained within the vial 200 resulting in an increased amount of sample 300 cells, cellular structures, related material, and other particulates to transfer from the collection apparatus to the vial, or like container, in order to increase diagnostic utility.

Embodiments are described with reference to FIGS. 1-7, wherein like numerals refer to like elements throughout. The terminology used in this description is not intended to be interpreted in any limited or restrictive manner; it is being utilized for illustrative purposes in conjunction with a detailed description of certain embodiments. Furthermore, embodiments may include several novel features, and no single feature is solely responsible for its desirable attributes or is essential to practicing the embodiments herein described.

Through various embodiments, a vial 200 is described by providing design features that address certain needs encountered in various cytology and related diagnostic methods. The foregoing description details certain embodiments. It will be appreciated, however, that no matter how detailed the foregoing appears in text, the described embodiments may be practiced in many other ways. As is also stated above, it should be noted that the use of particular terminology when describing certain features or aspects should not be taken to imply that the terminology is being re-defined herein to be restricted to including any specific characteristics of the features or aspects with which that terminology is associated.

What is claimed is:

1. A biological specimen collection vial kit comprising:
   a collection apparatus comprising any one of the group consisting of: a brush, a spatula, a swab, and a broom;
   a cap; and
   a vial consisting essentially of an external surface, a cap interface, a longitudinal axis and an interior surface, wherein the interior surface consists of a plurality of vertical interior surface features parallel to the longitudinal axis that are embedded on and proximate to the interior surface of the vial,
   wherein the vial is configured for physical agitation between the collection apparatus and one or more of said interior surface features in order to more effectively release cellular specimen material in to the vial.

2. The vial kit according to claim 1, wherein the interior surface features are arranged in a pattern on the interior of the vial and are spaced between 5 and 10 millimeters apart.

3. The vial kit according to claim 1, wherein the interior surface features are arranged in a pattern on the interior of the vial and are spaced more than 10 millimeters apart.

4. The vial kit according to claim 1, wherein the interior surface features are arranged in a vertical pattern on the interior of the vial and are spaced between 5 and 10 millimeters apart.

5. The vial kit according to claim 1, wherein the interior surface features are arranged in a vertical pattern on the interior of the vial and are spaced more than 10 millimeters apart.

6. The vial kit according to claim 1, wherein a cap is configured to be detached from the vial during processing of the sample.

7. The vial kit according to claim 1, wherein a cap is configured to not be detached from the vial during a sample collection, the cap comprising a hole in the top of the cap with a cover that allows the sample to be transferred into other containers for analysis.

8. A method of obtaining a biological sample disposed in a collection apparatus, the method comprising:
   contacting a collection apparatus with a vial, the collection apparatus selected among the group consisting of a brush, a swab, a spatula, and a broom, the vial comprising an interior surface, the interior surface consisting of a plurality of vertical interior surface features parallel to a longitudinal axis of, and located proximate to the interior surface of, the vial, wherein the collection apparatus contacts the vertical interior surface features in the vial in order to transfer the biological sample from the collection apparatus into the vial; and removing the collection apparatus from the vial.

9. The method of claim 8 further configured for harvesting cells and related cellular materials from the collection apparatus in a liquid-based system, further comprising the following steps:
   (a) providing the vial at least partially filled with liquid;
   (b) placing the collection apparatus in said vial so that a portion thereof is submerged in said liquid;
   (c) positioning said collection apparatus within said vial; and
   (d) moving said collection apparatus so that it physically contacts at least one of the interior surface features.

10. The method of claim 9, wherein said moving said collection apparatus so that it physically contacts at least one of the interior surface features comprises contact between said at least one of the interior surface features and said collection apparatus is selected among the group consisting of an endocervical brush, an endocervical swab, an endocervical spatula, and an endocervical broom.

11. The method of claim 8, further configured for harvesting cells and related cellular materials from the collection apparatus in a liquid-based system, further comprising the following steps:
   (a) providing the vial at least partially filled with liquid;
   (b) removing a cap from the vial;
   (c) placing the collection apparatus in said vial so that a portion thereof is submerged in said liquid;
   (d) positioning said collection apparatus within said vial;
   (e) moving said collection apparatus so that it physically contacts at least one of the interior surface features to increase the amount of a biological sample that can be obtained from the collection apparatus; and
   (f) replacing the cap on the vial.

12. The method of claim 8, further configured for harvesting cells and related cellular materials from the collection apparatus in a liquid-based system, further comprising the following steps:
   (a) providing the vial at least partially filled with liquid;
   (b) opening a cap from the vial;
   (c) placing the collection apparatus in said vial so that a portion thereof is submerged in said liquid;
   (d) positioning said collection apparatus within said vial;
   (e) moving said collection apparatus so that it physically contacts at least one of the interior surface features to increase the amount of a biological sample that can be obtained from the collection apparatus; and
   (f) closing the cap on the vial.

13. The method of claim 8, wherein the contacting the collection apparatus with the vial comprises contact between the collection apparatus and the vertical interior surface features, wherein the vertical interior surface features are selected from the group consisting of ribs, protrusions, depressions, wings, projections, surface finishes, friction surfaces, and meshes.

* * * * *